United States Patent [19]

Burolla et al.

[11] Patent Number: 4,865,090
[45] Date of Patent: Sep. 12, 1989

[54] VIAL HOLDER

[75] Inventors: Victor P. Burolla, Livermore; David W. Cheng, Union City, both of Calif.

[73] Assignee: Beckman Instruments, Inc., Fullerton, Calif.

[21] Appl. No.: 188,244

[22] Filed: Apr. 29, 1988

[51] Int. Cl.$^4$ ............................................. B65B 35/56
[52] U.S. Cl. .................................... 141/165; 141/172; 141/275; 141/329; 141/330; 141/369; 141/372; 215/DIG. 8; 206/446; 206/528; 220/85 H; 604/905; 269/55; 269/287
[58] Field of Search ................. 604/20, 415, 403, 407, 604/405; 141/98, 144, 148–152, 165–176, 275–278, 329, 330, 369–372, 375–378, 27; 215/DIG. 8, 100; 206/446, 528; 220/85 H; 198/803.9; 269/55, 56, 58, 287, 217, 233, 254 R

[56] References Cited

U.S. PATENT DOCUMENTS

| | | | |
|---|---|---|---|
| 3,285,455 | 11/1966 | Pewitt | 220/410 |
| 3,386,480 | 6/1968 | Riesenberg | 141/149 |
| 3,390,891 | 7/1968 | Stichman | 269/254 R |
| 3,536,225 | 10/1970 | Pech | 220/410 X |
| 3,819,194 | 6/1974 | Grevich et al. | 141/369 X |
| 3,853,158 | 12/1974 | Whitty | 141/27 |
| 4,041,994 | 8/1977 | Horowitz et al. | 141/1 |
| 4,166,457 | 9/1979 | Jacobson et al. | 604/20 X |
| 4,383,422 | 5/1983 | Gordon et al. | 220/410 X |
| 4,517,851 | 5/1985 | Tice | 141/165 X |
| 4,614,515 | 9/1986 | Tripp et al. | 604/403 |

*Primary Examiner*—Ernest G. Cusick
*Attorney, Agent, or Firm*—William H. May; Paul R. Harder

[57] ABSTRACT

A vial holder for a septum closed vial is disclosed which vial holder enables automated vial insertion to and withdrawal from puncturing hypodermics for the removal of contents or the communication of electrodes to liquids within the sealed vial. The vial—a commercial item of manufacture—includes a cylindrical glass body closed at the bottom and terminating upwardly at a narrowed neck to an opening. The opening accommodates both a septum and a septum retaining cap. A vial holder having an inside vial containing cavity with inside dimension complementary to the outside dimension of the vial is disclosed. This vial holder is formed from elastic material such as semirigid commercially available plastics and is vertically slotted from an open top at least partially to and towards the bottom of the holder. The vial holder is provided at the open top with inwardly extending fingers which register to the outside of the narrow neck of the septum sealed vial. These inwardly extending fingers form together an annulus that traps the vial in the holder at the narrow neck portion of the vial. The bottom of the vial holder is provided with a narrow shaft terminating at a depending boss.

13 Claims, 2 Drawing Sheets

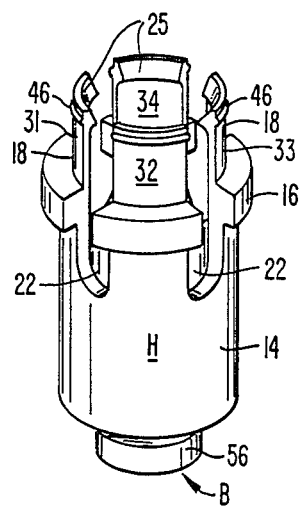
FIG._1.
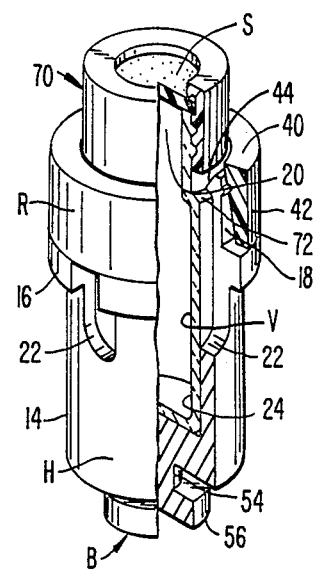
FIG._2.
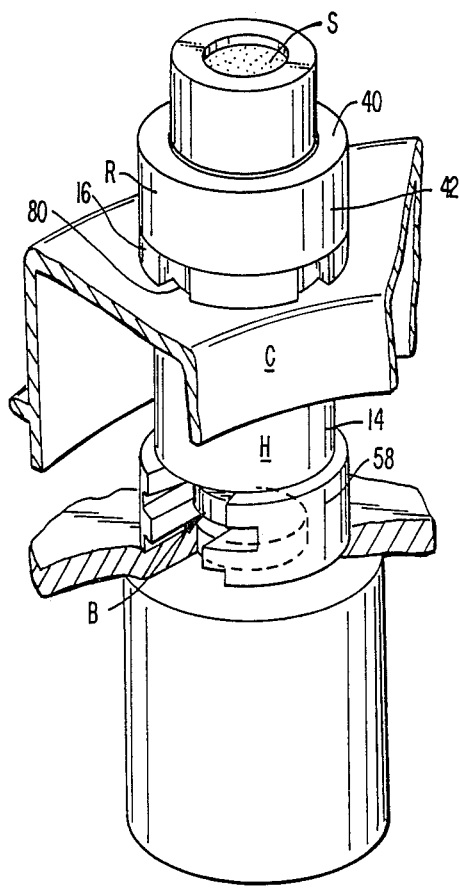
FIG._3.
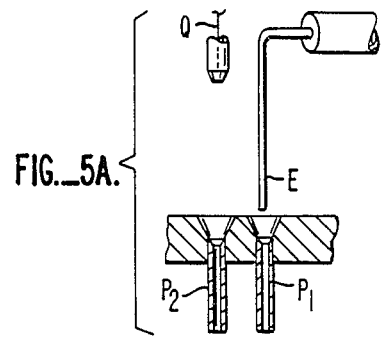
FIG._5A.
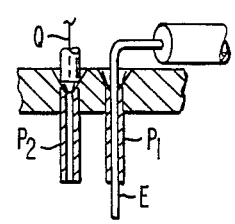
FIG._5B.

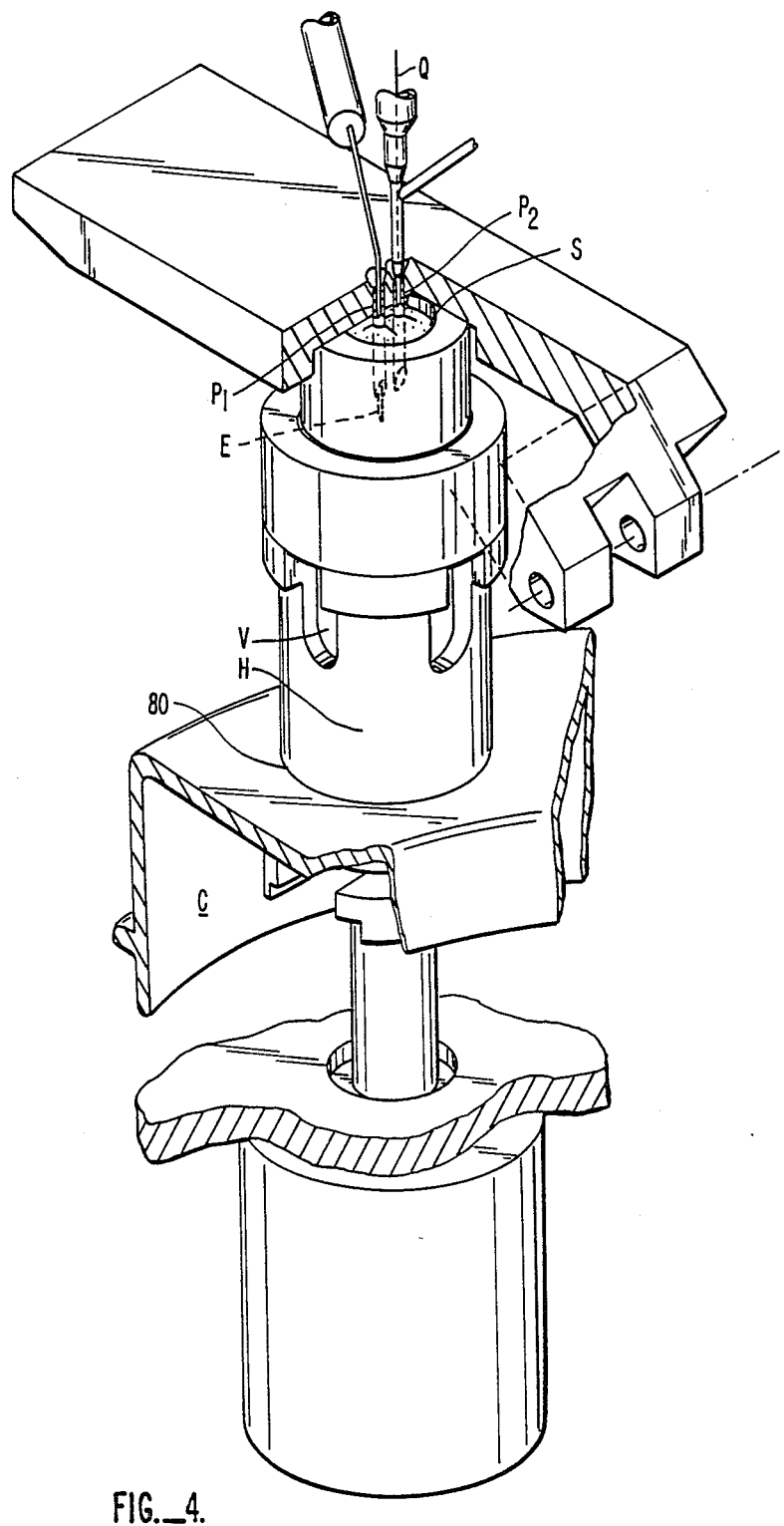
FIG._4.

VIAL HOLDER

BACKGROUND OF THE INVENTION

This invention relates to the automated manipulation of vials sealed by septums. More particularly, an apparatus for grasping, manipulating, and thereafter extracting or processing the contents of a septum sealed vial is disclosed.

SUMMARY OF THE PRIOR ART

Vials having narrowed necks with their tops sealed by septums are known. The septums are tightly held to the top of the bottle with septum retaining caps. Such caps expose the septums at the top in a circular area.

It is common to obtain access to the contents of such vials by hypodermic syringes. Typically, the hypodermic on the end of the syringe is manipulated to pierce the septum. The hypodermic penetrates the septum and is thereafter inserted below the level of liquid within the vial. Thereafter, by manipulation of the syringe to draw a vacuum on the hypodermic needle, fluid interior of the vial is withdrawn.

Statement of the Problem

It has become desirable to automatically penetrate and thereafter obtain access to the contents of vials having septum enclosed liquid such as electrolyte or samples. The septum ensures a sealed container until the moment of container use. The septum at the same time provides ready access to the contents of the vial by way of a hypodermic.

In automated electrophoresis there is a further necessity to extract samples from such vials. Further, and in order to induce capillary electrophoresis, it is necessary to introduce capillaries and electrodes into such septum sealed vials.

SUMMARY OF THE INVENTION

A vial holder for a septum closed vial is disclosed which vial holder enables automated vial insertion to and withdrawal from puncturing hypodermics for the removal of contents or the communication of electrodes to liquids within the sealed vial. The vial—a commercial item of manufacture—includes a cylindrical glass body closed at the bottom and terminating upwardly at a narrowed neck to an opening. The opening accommodates both a septum and a septum retaining cap. The cap holds the septum to seal the container and exposes an area of the septum for hypodermic puncture and access to the otherwise sealed vial contents. A vial holder having an inside vial containing cavity with inside dimension complementary to the outside dimension of the vial is disclosed. This vial holder is formed from elastic material such as semirigid commercially available plastics and is vertically slotted from an open top at least partially to and towards the bottom of the holder. The vial holder is provided at the open top with inwardly extending fingers which register to the outside of the narrow neck of the septum sealed vial. These inwardly extending fingers form together an annulus that traps the vial in the holder at the narrow neck portion of the vial. The bottom of the vial holder is provided with a narrow shaft terminating at a depending boss. In operation, the vial bottom is forced first into the vial holder so as to part elastically the inwardly extending annular fingers. When the vial fully penetrates the vial containing concavity of the vial holder, the fingers snap inwardly trapping the inserted vial at the narrowed neck within the vial holder. A retainer ring is then slipped over the top of the vial and the vial holder retaining fingers trapping the fingers from outward resilient movement and consequently trapping the vial within the holder. The vial is then placed to a conveyer and typically maneuvered so that the lower boss registers to boss holding apparatus. The vial holder is reciprocated relative to the conveyer by the boss holding apparatus grasping the boss. The boss then registers the vial at the septum to hypodermics. In the preferred embodiment, the hypodermics penetrate the septum and are threaded with capillaries and electrodes to enable the capillaries and electrodes to penetrate fluids such as sample and electrolyte sealed within the vial.

Other Objects, Features and Advantages

An object of this invention is to disclose a vial holder for a glass cylindrical vial having a restricted neck with septum sealed top. According to this aspect of the invention, a holder is fabricated from a semirigid elastic material. The holder is generally cylindrical so as to receive the glass vial and has an inside configuration complementary to the outside configuration of the vial to be held. The holder is slotted from the top partially towards the base. The glass vial is inserted with its glass base first and its restricted neck second and last. The top of the vial holder includes inwardly extending indentations on the finger describing a neck receiving annulus. When the vial registers with the holder with the narrow vial neck at the annulus, the fingers snap in and capture the vial at the neck. By the expedient of placing a cylindrical holder over the top of the neck to restrict resilient finger movement, the vial is securely fastened interior of the holder.

An advantage of the disclosed vial holder is that vials can be conveyed and manipulated from a conveyer to enable extraction of their contents. By the expedient of allowing a hypodermic to penetrate a septum, the contents of a vial will remain sealed until the moment of extraction.

A further object to this invention is to disclose the manipulation of a vial from a container by the vial holder. Accordingly, each vial holder is provided with a retaining boss. The retaining boss protrudes preferably concentrically at the bottom of the vial holder typically below a conveyor into which the vial holder is placed. A conveyor is provided with vial holder receiving apertures. These receiving apertures permit the retaining boss to depend downwardly of the conveyor and also permit reciprocal movement of the vial holder upwardly and downwardly relative to the conveyor. By the expedient of manipulating the retaining boss into registry with a boss retaining fitting and thereafter manipulating the boss retaining fitting upwardly and downwardly with respect to the conveyor, upward and downward manipulation of the vial occurs.

An advantage of this aspect of the invention is the vial can be automatically maneuvered to and from a penetrating hypodermic. Most importantly, the vial, when impaled at the septum on the hypodermic, can be easily removed from the hypodermic.

A further object of this invention is to disclose the immersion of a frail capillary or electrode into the contents of a vial sealed by a septum. According to this aspect of the invention, one or more hypodermic needles is positioned immediately above the vial. The vial is first conveyed into registry with the hypodermics. Thereafter, and through manipulation of the vial retaining boss, the vial is moved upwardly into a position of impalement of the hypodermics at the septum. Either during impalement or thereafter, a capillary or electrode is threaded through the opening created by the hypodermics. This threading permits the fluid in the vial to be exposed to current from the electrode as well as immersion of the capillary in the contents of the vial sealed septum.

An advantage of this aspect of the invention is that for the first time the contents of a septum sealed vial can either be remotely extracted to a frail capillary or alternatively contacted by an electrode. Particularly, the disclosed vial holder in combination with the hypodermics is particularly useful in automated capillary electrophoresis.

BRIEF DESCRIPTION OF THE DRAWINGS

Other objects, features, and advantages of this invention will become more apparent after referring to the following specification and attached drawings in which:

FIG. 1 is a perspective view of vial holder;

FIG. 2 is a perspective similar to FIG. 1 with the septum sealed vial contained within the holder and held in place by a retainer ring;

FIG. 3 illustrates the septum sealed vial within a conveyor being registered to a boss holding apparatus for up and down reciprocal movement of the vial relative to an aperture in a conveyor;

FIG. 4 illustrates a septum sealed vial being impaled at paired hypodermics for the side-by-side penetration of the vial with an electrode and a capillary to enable automated electrophoresis to occur from the interior of the septum sealed vial.

FIGS. 5A and 5B are respective views of the hypodermics being registered with respective electrodes and fluid receiving tubes (FIG. 5A) and later shown with the electrode and the fluid receiving tube respectively threading and receiving fluid from the vial (FIG. 5B).

DESCRIPTION OF THE PREFERRED EMBODIMENT

Referring to FIG. 1, a holder H is illustrated. Holder H comprises a cylinder 14 comprised of plastic having an upper ring 16. Protruding above upper ring 16 is a narrowed and elastic portion 18. As will hereinafter become more apparent, portion 18 is configured to provide a point of flexibility to the semirigid plastic of the holder H to enable the insertion and removal of a vial V. (See FIG. 2)

The top of vial V defines an opening 20. The holder H is provided with four slots 22. These slots being paced at 90° intervals around a cylindrical vial receiving aperture 24 defined within the vial holder.

The holder is configured to grasp the vial at the neck. Specifically, an inwardly extending annulus 25 is defined around the top portion of the vials.

It can be seen that the combination of the slots 22 and the inwardly extending annulus 25 impart to the vial four holding "fingers". These fingers are labeled 31 through 34.

Finally, there is provided a vial retaining ring R. (See FIG. 2) Ring R is provided with a shoulder 40 for resting on the top of the vial and a depending skirt 42. When a vial is within the holder, depending skirt 42 prevents the fingers from resiliently moving and opening. An inward annulus 44 captures a complementary annulus 46 on the fingers. A snapping of the ring into place on the end of the fingers occurs.

It is necessary that the bottom of the vial holder H be manipulated by a boss B. Specifically, a first shaft 54 having a concentric boss 56 is provided. Shaft 54 is narrower at boss 56 so that the conveyed vial holder registers to a holding appliance 58.

The operation of the vial holder is easy to understand with respect to FIG. 2. Specifically, a vial V having a septum S retained by a cap 70 is shown inserted fully within the holder H. The vial V is captured at neck 72 by inwardly extending annulus 25. Retainer ring R is shown sliding over the vial to effect full containment.

It can be seen from the view of FIG. 2 that vials can readily be removed and reinserted. By the expedient of removing the ring R, the vial becomes detachably removable. Specifically, the vial can be pulled upwardly biasing the discrete fingers 31–34 outwardly. Insertion constitutes the inverse of removal.

Referring to FIG. 3, a conveyor C having a group of cylindrical apertures 80 is illustrated. The conveyor C is shown conveying a vial holder into registry with a boss holding appliance 58. As shown in FIG. 3, boss holding appliance 58 has boss B registered within it.

Once such registry has occurred and as illustrated in FIG. 4, vial V is moved upwardly upon upward movement of boss B. Aperture 80 within the conveyor C forms a guide. Boss B is the point at which the vial is moved upwardly. As can be seen, hypodermics P1 and P2 are piercing the septum S of the vial V. At the same time, these respective septums are shown threaded with a capillary Q and an electrode E.

It can therefore be seen that the disclosed vial holder has many advantages. Specifically, and for the first time, vials are rendered removably detachable from a holding apparatus. By the expedient of manipulating the holding apparatus relative to a conveyor, access to the septum contained contents is readily generated.

What is claimed is:

1. A vial holder for a septum closed vial, a septum closed vial having a cylindrical glass body with a closed bottom and a narrowed open neck, said narrowed neck having a cap retaining a septum thereon, said vial holder comprising:

a holder body defining a bottom interior concavity having an inside configuration complementary to the outside configuration of said vial;

said concavity open at the top portion thereof;

a plurality of discrete resilient fingers extending from the bottom interior concavity of said holder body to and towards the top of said holder body;

an inwardly extending annulus defined at the upper end of said fingers, said inwardly extending annulus being configured complementary to the narrowed neck of said vial whereby a vial placed within said holder is held by said annulus at said neck;

a removable retaining ring for placement over said holder to enable retention of said vial.

2. The invention of claim 1 and wherein said removable retaining ring defines a first annulus;

said discrete resilient fingers define a second annulus for mating to said first annulus; and said first and second annulus resiliently coact for maintaining said ring to said vial holder.

3. The invention of claim 1 and including a boss extending downwardly from the bottom of said holder body, said boss attached centrally to said holder body whereby said vial holder may be manipulated from said boss.

4. A vial and vial holder in combinations comprising;

a cylindrical glass vial;

a narrowed neck at the top of said glass vial, said neck defining an opening and a cap receiving lip at the upper portion thereof;

a septum closing said vial;

a cap holding said septum on said vial over said neck and exposing a portion of said septum for puncture and access to the contents of said vial;

a vial holder, said vial holder having a member of semirigid material defining a vial receiving interior, said vial receiving interior being complementary in inside dimension to the exterior dimension of said vial;

a plurality of resilient fingers configured from the bottom of said vial holder to and towards the top thereof;

said resilient fingers of said vial holder defining inwardly extending annulus for complementary fitting with the neck of said vial whereby a vial placed within said holder registers to said inwardly extending fingers to capture said vial at said neck;

a retainer ring for movement over said fingers with said captured vial therein to prevent movement of said resilient fingers whereby removal of said vial in said holder is inhibited.

5. The invention of claim 4 and including a protruding boss from the bottom of said vial holder for manipulation of said vial whereby said vial holder and vial can be manipulated by grasping said boss.

6. The invention of claim 4 and wherein said retainer ring is removably attachable over said vial holder.

7. The invention of claim 4 and wherein said vial holder is slotted at four equal angular intervals on said vial holder to define said resilient fingers.

8. A septum sealed vial, vial holder and conveyor comprising in combination;

a cylindrical glass vial;

a narrow neck at the top of said glass vial, said neck defining an opening and a cap receiving lip at the upper portion of said opening;

a septum closing said vial;

a cap holding said septum on said top of said glass vial and exposing a portion of said septum for puncture and access to the contents of said vial;

a vial holder, said vial holder having a member of semirigid material defining a bottom vial receiving interior, said bottom vial receiving interior being complementary in inside dimension to the exterior dimension of said vial;

a plurality of resilient figures attached to the bottom vial receiving interior of said vial holder and extending to the sides of said vial holder to and towards the top thereof;

said resilient figures of said vial holders defining inwardly extending annular members for complementary fitting with the neck of said vial whereby a vial placed within said holder registers to said inwardly extending annular members to capture said vial at said neck;

a retainer ring for movement over said fingers with said captured vial therein to prevent movement of said resilient fingers whereby removal of said vial in said holder is inhibited;

a conveyor;

an aperture in said conveyor for defining a spatial interval permitting sliding movement of said vial relative into said aperture in said conveyor; and, means for manipulating said vial holder relative to said conveyor protruding downwardly from the bottom of said vial to enable selective up and down movement of vial with respect to said conveyor.

9. The invention of claim 8 and wherein said means for manipulating said vial includes a boss affixed to the bottom of said vial holder.

10. The invention of claim 9 and including a hypodermic overlying said conveyor;

means for manipulating said vial to and from a position of impalement on said hypodermic whereby said hypodermic obtains access to the contents of said vial.

11. Apparatus for penetrating a septum sealed vial with a member lacking stiffness to penetrate said septum, a vial including a cylindrical glass vial, a narrowed neck defined at the top of said vial, said neck defining an opening and cap receiving lip at the upper portion thereof; a septum closing said vial; a cap exposing said septum as closing said vial over said neck, said septum disposed for puncture and access to the contents of said vial; said apparatus comprising:

a vial holder, said vial holder having a member of semirigid material defining a bottom vial receiving interior, said bottom vial receiving interior being complementary in inside dimension to the exterior dimension of said vial;

a plurality of resilient fingers attached to the bottom vial receiving interior of said vial holder and towards the top thereof;

said resilient fingers of said holder defining inwardly extending annular members for complementary fitting with said narrowed neck of said vial whereby a vial placed within said holder registers to said inwardly extending fingers to capture said vial at said neck;

a retainer ring for movement over said fingers with said captured vial therein to prevent movement of said resilient fingers whereby removal of said vial in said holder is inhibited;

a conveyor for conveying said vial holder, said conveyor permitting relative upward and downward movement of said vial holder with respect to said conveyor;

means for manipulating said vial from under said conveyor for causing upward and downward reciprocal movement of said vial;

a hypodermic overlying said vial for impaling said vial at said septum;

and a member lacking stiffness to penetrate said septum, said member depending downwardly through said hypodermic, said member fitted interiorly of said hypodermic and having a length whereby when said vial is moved upwardly said member can be immersed within liquid contents contained within said vial.

12. The invention of claim 11 and wherein said member lacking stiffness to penetrate said septum is a capillary.

13. The invention of said claim 11 and wherein said member lacking stiffness to penetrate said septum is an electrode.

* * * * *